(12) United States Patent
Magnusson et al.

(10) Patent No.: US 11,129,748 B2
(45) Date of Patent: Sep. 28, 2021

(54) CURVED EYE PROTECTION SHIELD FOR WELDING PROTECTION

(71) Applicant: 3M INNOVATIVE PROPERTIES COMPANY, St. Paul, MN (US)

(72) Inventors: Kristina M. Magnusson, Djurmo (SE); Kenneth Jarefors, Borlänge (SE); Laurent Froissard, Cranston, RI (US); Britton G. Billingsley, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 115 days.

(21) Appl. No.: 16/098,155

(22) PCT Filed: May 1, 2017

(86) PCT No.: PCT/US2017/030344
§ 371 (c)(1),
(2) Date: Nov. 1, 2018

(87) PCT Pub. No.: WO2017/192421
PCT Pub. Date: Nov. 9, 2017

(65) Prior Publication Data
US 2019/0142640 A1     May 16, 2019

(30) Foreign Application Priority Data
May 4, 2016 (EP) ..................... 16168229

(51) Int. Cl.
   *A61F 9/06* (2006.01)
(52) U.S. Cl.
   CPC .............. *A61F 9/061* (2013.01); *A61F 9/06* (2013.01); *A61F 9/067* (2013.01)

(58) Field of Classification Search
CPC . A61F 9/061; A61F 9/06; A61F 9/067; G02B 5/20; G02B 13/18; G02C 7/068
See application file for complete search history.

(56) References Cited

U.S. PATENT DOCUMENTS

| | | | |
|---|---|---|---|
| 2,628,530 | A | 2/1953 | Rabben |
| 4,039,254 | A | 8/1977 | Harsch |

(Continued)

FOREIGN PATENT DOCUMENTS

| | | |
|---|---|---|
| CN | 2321028 U | 5/1999 |
| DE | 19624882 | 1/1998 |

(Continued)

OTHER PUBLICATIONS

International Search report for PCT International Application No. PCT/US2017/030344 dated Oct. 9, 2017, 5 pages.

(Continued)

*Primary Examiner* — Khoa D Huynh
*Assistant Examiner* — Erick I Lopez
(74) *Attorney, Agent, or Firm* — Gregg H. Rosenblatt

(57) ABSTRACT

A curved eye protection shield for welding protection. The eye protection shield has an electrically switchable darkening filter and a protective cover. The darkening filter has eye facing major inner and outer surfaces, and the protective cover has major inner and outer surfaces. The protective cover is provided for arrangement on the inner surface of the darkening filter. The inner and outer surface of the darkening filter are equidistant, whereas the inner and outer surface of the protective cover are non-equidistant. The invention is advantageous in that it provides an eye protection shield having a minimized refractive power.

12 Claims, 1 Drawing Sheet

(56) References Cited

U.S. PATENT DOCUMENTS

| | | |
|---|---|---|
| 4,185,328 A | 1/1980 | Graveno |
| 4,240,709 A | 12/1980 | Hornell |
| 4,373,212 A | 2/1983 | West |
| 4,649,571 A | 3/1987 | Falkiner |
| 5,302,815 A | 4/1994 | Eggenschwiler |
| 5,793,449 A | 8/1998 | Lagerwall |
| 5,815,848 A | 10/1998 | Jarvis |
| 5,854,667 A | 12/1998 | Ackermann |
| 5,857,215 A | 1/1999 | Fergason |
| 5,959,705 A * | 9/1999 | Fergason ............ B23K 9/32 2/8.8 |
| 6,009,564 A | 1/2000 | Tackles |
| 6,038,705 A | 5/2000 | Jarvis |
| 6,151,711 A | 11/2000 | Edwards |
| 6,401,244 B1 | 6/2002 | Kramer |
| 6,412,945 B1 | 7/2002 | Grove |
| 6,557,174 B2 | 5/2003 | Martin |
| 6,715,150 B1 | 4/2004 | Potin |
| 6,893,126 B2 | 5/2005 | Iori |
| 7,284,281 B2 | 10/2007 | Huh |
| 7,389,543 B2 | 6/2008 | Reichow |
| 7,419,261 B2 | 9/2008 | Dumange |
| D616,155 S | 5/2010 | Juhlin |
| 7,901,074 B2 | 3/2011 | Yamamoto |
| 8,081,262 B1 | 12/2011 | Perez |
| 8,677,517 B1 | 3/2014 | Morency |
| 8,797,236 B2 | 8/2014 | Seo |
| 8,806,662 B2 | 8/2014 | Huh |
| 8,990,963 B2 | 3/2015 | Matthews |
| 8,990,964 B2 | 3/2015 | Anderson |
| 9,038,198 B2 | 5/2015 | Feinberg |
| 9,364,718 B1 * | 6/2016 | Tracy ............ G02C 7/02 |
| 9,557,568 B1 | 1/2017 | Ouderkirk et al. |
| 2007/0089215 A1 | 4/2007 | Biche |
| 2009/0051834 A1 | 2/2009 | Cottier |
| 2014/0007312 A1 * | 1/2014 | Wright ............ A61F 9/06 2/8.2 |
| 2014/0013479 A1 | 1/2014 | Magnusson |
| 2014/0092328 A1 | 4/2014 | Werthmuller et al. |
| 2014/0168546 A1 * | 6/2014 | Magnusson ............ G02F 1/1333 349/14 |
| 2015/0001378 A1 | 1/2015 | Magnusson |
| 2016/0081856 A1 | 3/2016 | Hofer-Kraner |

FOREIGN PATENT DOCUMENTS

| | | |
|---|---|---|
| DE | 10123247 | 11/2002 |
| DE | 202009004207 | 6/2009 |
| GB | 136263 | 12/1919 |
| GB | 935467 | 8/1963 |
| GB | 2225646 | 6/1990 |
| KR | 101178254 | 2/2012 |
| KR | 101481980 | 12/2014 |
| KR | 200476077 | 1/2015 |
| WO | WO 2009-056608 | 5/2009 |
| WO | WO 2012-074895 | 6/2012 |
| WO | WO 2014-092989 | 6/2014 |
| WO | WO 2016/037544 A1 | 3/2016 |

OTHER PUBLICATIONS

Search Report for CN Appl. No. 201780027634.8, dated Apr. 24, 2020, 1 pg.

Search Report for AU Appl. No. 2019283838, dated Jun. 25, 2020, 5 pp.

* cited by examiner

CURVED EYE PROTECTION SHIELD FOR WELDING PROTECTION

CROSS REFERENCE TO RELATED APPLICATIONS

This application is a national stage filing under 35 U.S.C. 371 of PCT/US2017/030344, filed May 1, 2017, which claims the benefit of European Application No. 16168229.9, filed May 4, 2016, the disclosure of which is incorporated by reference in its/their entirety herein.

FIELD OF THE INVENTION

The invention relates to a curved eye protection shield for welding protection, and in particular to a curved eye protection shield which comprises an electrically switchable darkening filter having two equidistant major surfaces, and a protective cover having two non-equidistant major surfaces.

BACKGROUND ART

Automatic darkening filters commonly have a switchable filter that automatically changes from a light-transmission-state to a dark-transmission-state in response to incident light. The switching is generally achieved through use of a photodetector that is located on, or as part of, personal protective equipment. The photodetector recognizes the presence of the incident light-to-be-filtered, and an electronic module generates a control voltage that, when applied to the switchable filter, causes the filter to change from the light-transmission-state to the dark-state.

Automatic light filters have been designed which contain liquid-crystal cells located between polarizing films. U.S. Pat. No. 4,240,709 to Hornell describes a switchable filter that has a single-twisted, nematic, liquid-crystal cell sandwiched between a pair of mutually crossed polarizers. The liquid-crystal cells are optically-transparent glass substrates that include transparent electrode and alignment layers. The liquid-crystal molecules orientate themselves in a particular direction when a voltage is applied across the liquid-crystal cell under the control of an electronic module. Many commercially available products use this kind of switchable filter.

The use of an automatic-darkening filter in a protective shield gives significant ergonomic benefits. Previously welders, for example, had to "nod" their welding shield down when they struck the welding arc to ensure that their eyes were protected from the torch light. Automatic welding filters eliminate this action since the welding shield can be left in position continuously.

SUMMARY OF THE INVENTION

The invention relates to a curved eye protection shield for welding protection. The eye protection shield comprises an electrically switchable darkening filter and a protective cover. The darkening filter has an eye facing major inner surface and a major outer surface. The inner surface and the outer surface of the darkening filter are opposite of each other, meaning facing in opposite directions. Further, the protective cover has a major inner surface and further a major outer surface. The inner surface and the outer surface of the protective cover are opposite of each other, meaning facing in opposite directions. The protective cover may be arranged relative to the darkening filter directly on or spaced adjacent the outer surface of the darkening filter, or on or spaced adjacent the inner surface of the darkening filter. Accordingly, the outer surface of the protective cover faces the inner surface of the darkening filter or, alternatively, the inner surface of the protective cover faces the outer surface of the darkening filter. The inner and outer surface of the darkening filter are equidistant, whereas the inner and outer surface of the protective cover are non-equidistant. The electrically switchable darkening filter therefore has two equidistant major surfaces, and the protective cover has two non-equidistant major surfaces.

Because the inner and outer surface of the darkening filter being equidistant the portion of the darkening filter formed by the inner and outer surface has a uniform thickness (defined between the inner and outer surface of the darkening filter). Further, because the inner and outer surface of the protective cover being non-equidistant the portion of the protective cover formed by the inner and outer surface has a non-uniform thickness (defined between the inner and outer surface of the protective cover).

The invention is advantageous in that it provides for a curved eye protection shield having no or a minimized refractive power. Further, the invention allows for compensating a refractive power of a curved darkening filter. The invention further provides for a maximized convenience for a wearer of a welding protector having a curved darkening filter, in providing an eye protector with minimized refractive power.

For the purpose of the present specification the term "equidistant" refers to two curves or surfaces which extend at the same distance relative to each other along their length or across their areas, respectively. For example two equidistant planes are parallel to each other.

Preferably the darkening filter is switchable between a light-transmission-state in which a substantial portion of light can pass through the darkening filter and a dark-state in which a substantial portion of light is blocked from passing through the darkening filter. In the light-transmission-state the transmittance of the darkening filter may be within a range of about 1% to about 20%, in more particular within a range of about 5% to about 10%, whereas in the dark-state the transmittance of the darkening filter may be within a range of about 0.0005% to about 0.1%.

In one embodiment the inner and outer surface of the darkening filter are cylindrical and concentric relative to each other. The inner and outer surface of the darkening filter preferably form surfaces of a portion of the darkening filter which serve for the user, for example a welder, to see through during use. This portion of the darkening filter therefore may also be referred to as the "see-through portion of the darkening filter". The darkening filter may have further portions, such as one or more structures for stiffening the darkening filter or for mounting the darkening filter within the eye protection shield, for example. Such further portions are typically not used for seeing through and further may not have equidistant inner and outer surfaces.

Preferably, the inner and outer surface of the protective cover are cylindrical. However, the cylinder shape of both, the inner and outer surface of the protective cover, are preferably in an off-center relationship to each other. The cylindrical shape of the inner and outer surface of the protective cover may have the same radius. Again, the inner and outer surface of the protective cover preferably form surfaces of a portion of the protective cover which serve for the user, for example a welder, to see through during use. This portion of the protective cover therefore may also be referred to the "see-through portion of the protective cover".

The protective cover may have further portions, such as one or more structures for stiffening the protective cover or for mounting the protective cover within the eye protection shield, for example. Such further portions are typically not used for seeing through.

In a further embodiment the protective cover is pre-shaped so that the outer surface of the protective cover corresponds in shape to the inner surface of the darkening filter. Further, the protective cover may be pre-shaped so that the outer surface of the protective cover corresponds to a proportionally reduced shape of the inner surface of the darkening filter. Such a proportionally reduced shape may be provided to account for a space between the darkening filter and the protective cover. For example, the radius of the outer surface of the protective cover may be smaller than the radius of the inner surface of the darkening filter. Further, the darkening filter and the protective cover may be arranged relative to each other such that the inner surface of the darkening filter and the outer surface of the protective cover are concentric. Accordingly, the space between the inner surface of the darkening filter and the outer surface of the protective cover has a uniform thickness.

In an alternative embodiment, the protective cover is pre-shaped so that the inner surface of the protective cover corresponds in shape to the outer surface of the darkening filter. Further, the protective cover may be pre-shaped so that the inner surface of the protective cover corresponds to a proportionally enlarged shape of the outer surface of the darkening filter. Such a proportionally enlarged shape may be provided to account for a space between the darkening filter and the protective cover. For example, the radius of the inner surface of the protective cover may be greater than the radius of the outer surface of the darkening filter. Further, the darkening filter and the protective cover may be arranged relative to each other such that the outer surface of the darkening filter and the inner surface of the protective cover are concentric. Accordingly, the space between the outer surface of the darkening filter and the inner surface of the protective cover has a uniform thickness.

For example, the protective cover may be molded (for example injection molded) from an optically clear plastic material. The inner and outer surface of such a molded protective cover preferably naturally has the cylindrical shape, in particular without being under mechanical tension.

In one embodiment the protective cover has a first thickness adjacent a margin and a second thickness in the middle between two opposite margins. The margins preferably refer to lateral margins of the see-through portion. The lateral ends of the see-through portion are opposite ends in a horizontal dimension of the eye protection shield. The term "horizontal" refers to a dimension of the eye protection shield that is defined by a parallel to the centers of the wearer's eyes, when the eye protection is worn by a wearer. Further the eye protection shield has a vertical dimension. The term "vertical" refers to a dimension perpendicular the horizontal dimension and perpendicular to the optical axis of the wearer's eyes in a straight view orientation. The first and second thickness each are preferably uniform along the vertical dimension.

The second thickness is preferably greater than the first thickness. The thickness of the protective cover gradually increases from the first toward the second thickness. The second thickness may be within a range of about 1 mm to 3 mm, preferably 1.7 mm or about 1.7 mm.

In one embodiment the cylindrical shape of the inner and outer surface of the protective cover are based on the same radius. The radius may be within a range of 70 mm to 150 mm, more preferably within a range of 80 mm to 100 mm, most preferably 85 mm or about 85 mm. Further, the center axes of the cylindrical shape of each the inner and outer surface of the protective cover are preferably parallel offset from each other on a normal on the inner and outer surface. Preferably the offset is within a range of 0.5 mm to 3 mm, more preferably 1.7 mm or about 1.7 mm.

In one embodiment the protective cover is removably attached to the darkening filter. The darkening filter and the protective cover are preferably arranged with a (preferably uniform) space between the inner surface of the darkening filter and the outer surface of the protective cover. Alternatively, the darkening filter and the protective cover are arranged with a (preferably uniform) space between the outer surface of the darkening filter and the inner surface of the protective cover. The eye protection shield may comprise a spacer for providing such a space. The spacer may be formed by one or more protrusions (for example a circumferential rim or circumferentially distributed pins) that is/are arranged adjacent a margin of the inner or outer surface of the darkening filter or adjacent a margin of the inner or outer surface of the protective cover. Further, the protective cover may be mounted in a welding protector in which also the darkening filter is integrated. The protective cover may in this embodiment mounted at a space relative to the darkening filter. Alternatively, the darkening filter and the protective cover may, for example, be bonded to each other by an optically clear adhesive.

For the purpose of the present specification any surface of the spacer does not form part of the inner or outer surface of the darkening filter and/or the protective plate, although the spacer may be monolithically formed with the darkening filter and/or the protective cover.

In one embodiment the protective cover is made of a plastic material selected from among polycarbonate (PC), polymethyl methacrylate (PMMA), polystyrene (PS) and styrene acrylonitrile copolymer (SAN). Preferably, the protective cover is molded, in particular injection molded, in the cylindrical shape. In more particular, the protective cover may be molded, in particular injection molded, such that the inner and outer surface are in the cylindrical shape.

In a further embodiment the darkening filter comprises liquid crystals arranged in direct contact between a first and second alignment layer, the first and second alignment layer being arranged on a first and a second transparent electrode layer, respectively, and the first and second transparent electrode layer are arranged on a first and a second transparent layer, respectively, and wherein the first and a second transparent layer are each provided with a polarizer. The first and second transparent layer, first and second electrode layer and first and second alignment layer form a liquid crystal cell. In a preferred embodiment the eye protection shield comprises two liquid crystal cells arranged in optical sequence. This means that a light beam impinging on perpendicular on the eye protection shield passes both liquid crystal cells at least in the light-transmission-state. In such an embodiment one polarizer may be arranged between the two liquid crystal cells and the so formed sandwich of the two liquid crystal cells may be arranged between further two polarizers. Accordingly, such an embodiment has three polarizers and two liquid crystal cells. This is advantageous to provide a maximized darkening effect in the dark-state and a sufficient light transmission state in the light-transmission-state.

The eye protection shield is preferably connected to a sensor and a control circuit. In particular, the control circuit is preferably electrically connected to the first and second electrode layer of the liquid crystal cell for powering liquid crystal cell dependent on a signal provided by the sensor. The control circuit may for example apply a voltage to the first and second electrode layer for causing the liquid crystals to orient in a particular orientation, or switch off the voltage so that the liquid crystals reset to their preferred orientation provided by the first and second alignment layer. Thereby the darkening filter is switched between the light-transmission-state or the dark-state. Preferably, the sensor, the control circuit and the darkening filter cooperate such that light of a certain minimum intensity received by the sensor causes the darkening filter to switch in the dark-state, and light of an intensity below that minimum intensity causes the darkening filter to switch in the light-transmission-state.

In a further embodiment the eye protection shield has a band pass filter for attenuating the infra-red (IR) and ultra-violet (UV) wavelength components from high-intensity incident light. The band pass filter can be an interference filter that reflects the IR radiation and absorbs the UV-A, -B and -C components of the incident light.

In one embodiment the curved eye protection shield the protective cover is an "inner protective cover". The inner protective cover is arranged with the outer surface facing the inner surface of the darkening filter. Alternatively, the protective cover may be an "outer protective cover". The outer protective cover is arranged with the inner surface facing the outer surface of the darkening filter. It is noted that the invention encompasses an eye protection shield having both, an inner and an outer protective cover. In other words, the presence of an inner protective cover does not exclude the additional presence of an outer protective cover.

In such an embodiment the outer protective cover may have non-equidistant inner and outer surfaces as described above or equidistant inner and outer surfaces as described in the following.

Accordingly, in one embodiment the eye protection shield further (in addition to the inner protective cover having non-equidistant inner and outer surfaces) has an outer protective cover being arranged on or adjacent the outer surface of the darkening filter. The outer protective cover may be provided to protect the darkening filter from dust and splashes of hot or glowing material during welding. Preferably, the outer protective cover is removably attached to the darkening filter. Therefore, the outer protective cover can be replaced if necessary. The outer protective cover may have a major inner surface and, opposite thereof, a major outer surface. The inner and outer surface of the outer protective cover may be equidistant. In other words a thickness defined between the inner and outer surface of the outer protective cover is preferably uniform. The inner and outer surface of the outer protective cover preferably form surfaces of a portion of the outer protective cover which serve for the user, for example a welder, to see through during use. This portion of the outer protective cover therefore may also be referred to the "see-through portion of the outer protective cover". The outer protective cover may have further portions, such as one or more structures for stiffening the outer protective cover or for mounting the outer protective cover within the eye protection shield, for example. Such further portions are typically not used for seeing through and further may not have equidistant inner and outer surfaces.

Alternatively, in one embodiment the eye protection shield further (in addition to the outer protective cover having non-equidistant inner and outer surfaces) has an inner protective cover being arranged on or adjacent the inner surface of the darkening filter. Again, the inner protective cover may be provided to protect the darkening filter from dust and splashes of hot or glowing material during welding. Preferably, the inner protective cover is removably attached to the darkening filter. Therefore, the inner protective cover can be replaced if necessary. The inner protective cover may have a major inner surface and, opposite thereof, a major outer surface. The inner and outer surface of the inner protective cover may be equidistant. In other words a thickness defined between the inner and outer surface of the inner protective cover is preferably uniform. The inner and outer surface of the inner protective cover preferably form surfaces of a portion of the inner protective cover which serve for the user, for example a welder, to see through during use. This portion of the inner protective cover therefore may also be referred to the "see-through portion of the inner protective cover". The inner protective cover may have further portions, such as one or more structures for stiffening the inner protective cover or for mounting the inner protective cover within the eye protection shield, for example. Such further portions are typically not used for seeing through and further may not have equidistant inner and outer surfaces.

The refractive power for the purpose of the present specification is measured in accordance with Standards EN 166:2001 (E) and EN 167:2001 (E).

In a further aspect the invention relates to a welding protector. A welding protector may be a welding mask or welding helmet, for example. The welding protector preferably comprises the curved eye protection shield of the invention and a non-transparent head protection shield. The head protection shield preferably at least comprises a face protection portion. The head protection shield may comprise a further portion for protecting further parts of a wearer's head. The head protection shield preferably forms a window which is closed by the curved eye protection shield.

In a further embodiment the welding protector further comprises a headband for retaining the welding protector on a wearer's head. The head protection shield is preferably pivotally suspended relative to the headband. Thus, the head protection shield can be swiveled between a lower position in which the head protection shield protects a wearer's face, eyes and eventually further parts, and an upper position in which the head protection shield is lifted away from the wearer's face. Therefore a wearer does not need to put of the welding protector for accessing her or his face, for example.

In a further aspect the invention relates to a method of retrofitting a welding protector which has a curved eye protection shield. The eye protection shield comprises an electrically switchable darkening filter having an eye facing major inner surface and, opposite thereof, a major outer surface. The inner and outer surface of the darkening filter are equidistant. The method comprises the steps of (i) providing a protective cover having a major inner surface and further a major outer surface, wherein the inner and outer surface of the protective cover are non-equidistant (as specified herein), and (ii) mounting the protective cover relative to the darkening filter such that the outer surface of the protective cover faces the inner surface of the darkening filter or such that the inner surface of the protective cover faces the outer surface of the darkening filter.

DETAILED DESCRIPTION OF THE INVENTION

Figure 1:
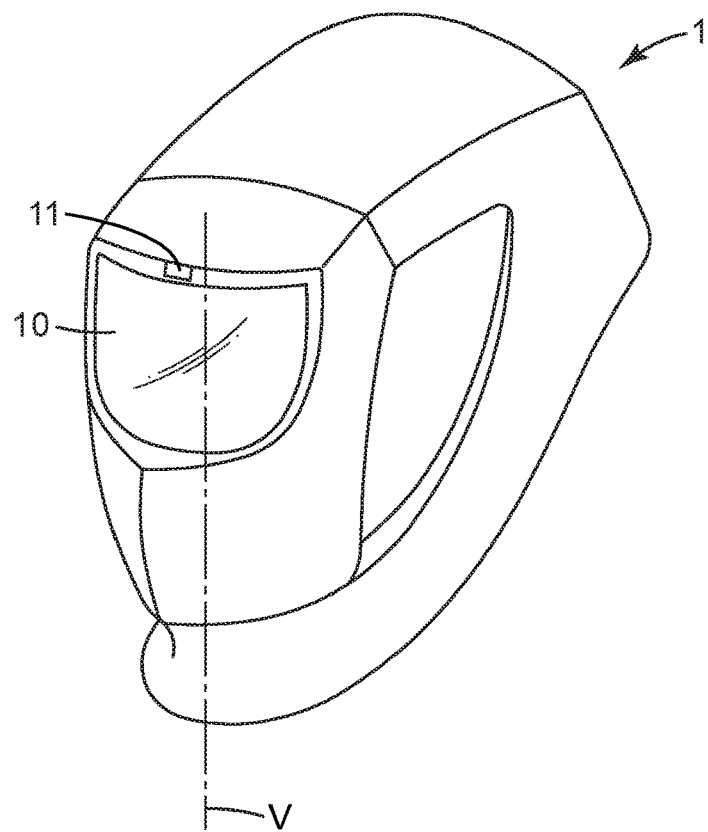
FIG. 1 is a perspective view of a welding protector according to an embodiment of the invention.
Figure 2:
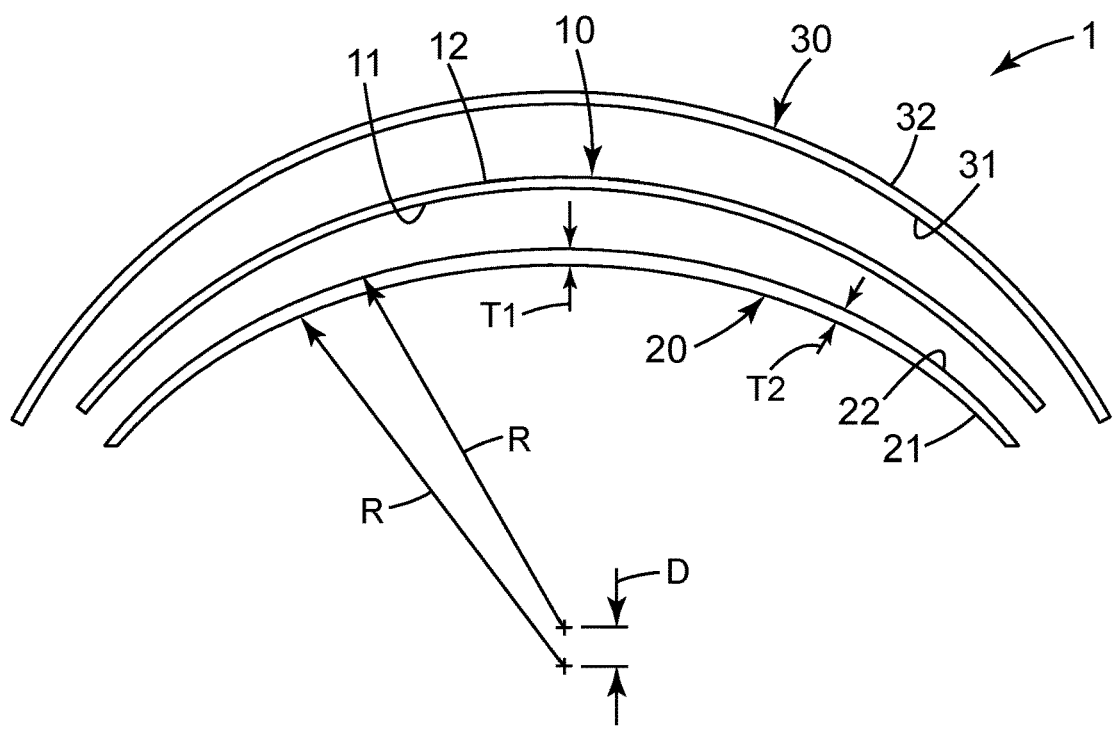
FIG. 2 is a top view on an eye protection shield according to an embodiment of the invention.

FIG. 1 shows a curved eye protection shield 1 for welding protection. The eye protection shield 1 has an electrically switchable darkening filter 10, an inner protective cover 20 and an outer protective cover 30.

The darkening filter 10 is an automatic darkening filter, in the example is based on a liquid crystal cell. The darkening filter 10 is electrically switchable between a light-transmission-state and a dark-state. When switched in the dark-state, the darkening filter 10 blocks a significant amount of light from being transmitted therethrough. This enables a user to observe a welding arc by seeing through the darkening filter 10 without risking to be exposed to harmful light radiation from the welding arc. In the light-transmission-state the darkening filter 10 permits a significant amount of light to be transmitted therethrough. Thus, the darkening filter 10 in the light-transmission-state allows the user to see under ambient light conditions (in the absence of the welding arc).

The darkening filter 10 has an eye facing major inner surface 11 and, opposite thereof, a major outer surface 12. Further, the inner protective cover 20 has a major inner surface 21 and further a major outer surface 22. The inner protective cover 20 is provided for arrangement on or next to the inner surface 11 of the darkening filter 10. In the example the inner protective cover 20 is attached at a space relative to the inner surface 11 of the darkening filter 10. Several ways of attaching the inner protective cover 20 to the darkening filter 10 are possible, for example by individually mounting the darkening filter 10 and the inner protective cover 20 in a welding protector (not illustrated).

The inner and outer surface 11, 12 of the darkening filter 10 are equidistant. In the example, the inner and outer surface 11, 12 of the darkening filter 10 each have a cylindrical shape. Therefore, the equidistant inner and outer surface 11, 12 are concentric relative to each other. Due to the curvature of the cylindrical shape the darkening filter 10 has a certain refractive power with respect to a wearer viewing through the darkening filter 10. This is because light passing through the darkening filter 10 at angles other than perpendicular to the inner and outer surface 11, 12 are deflected by the darkening filter 10.

The inner and outer surface 21, 22 of the inner protective cover 20 are non-equidistant. In particular the inner and outer surface 21, 22 are shaped to compensate for the refractive power of the darkening filter 10. In the example, the inner and outer surface 21, 22 are each cylindrical but not concentric. In particular, the inner and outer surface 21, 22 are in an off-center relationship relative to each other. The centers of the inner and outer surface 21, 22 of the inner protective cover 20 are offset relative to each other in a dimension perpendicular to the inner and outer surface 21, 22. Further, the inner and outer surface 21, 22 are arranged such that the center of the outer surface 22 is arranged between the center of the inner surface 21 and the inner protective cover 20. Accordingly, the inner and outer surface 21, 22 extend non-equidistant relative to each other, in a manner providing a refractive power that compensates for the refractive power of the darkening filer 10.

The outer protective cover 30 in the example has a major inner and a major outer surface 31, 32 which extend equidistant to each other. In particular, the inner and outer surface 31, 32 are cylindrical and concentric relative to each other. In another example the outer protective cover 30 may extend non-equidistant to compensate for a refractive power of the darkening filter 10. In still another example the refractive power of the darkening filter 10 may be compensated by a combination of both, the inner and outer protective cover 20, 30.

The outer surface 12 of the darkening filter 10 is based on a cylindrical shape which is defined by a radius of 90.1 mm and the inner surface 11 of the darkening filter 10 is based on a cylindrical shape which is defined by a radius of 89 mm. The inner and outer surface 11, 12 of the darkening filter 10 are concentric. The refractive power of the darkening filter 10 is −0.044 l/m. The inner and outer surface 21, 22 of the inner protective cover 20, are each based on a cylindrical shape which is defined by a radius R of 85 mm. The inner and outer surface 11, 12 are in an off-center relationship to each other with the offset D of the off-center relationship being 1.7 mm. Accordingly, the maximum thickness T1 is 1.7 mm. T2 indicates an area in which the inner protective cover has a smaller thickness than 1.7 mm. The refractive power of the inner protective cover 20 in the example is 0.051 l/m. Further, in this embodiment the outer surface 32 of the outer protective cover 30 is based on a cylindrical shape which is defined by a radius of 91 mm and an inner surface 31 of the outer protective cover 30 is based on a cylindrical shape which is defined by a radius of 90.25 mm. The inner and outer surface of the outer protective cover are concentric. The refractive power of the outer protective cover is −0.034 l/m. The combination of the inner protective cover 20, the darkening filter 10 and the outer protective cover 30 (as illustrated) thus has a total refractive power of −0.027 l/m. The absolute value of the total refractive power of the combination of the inner protective cover 20, the darkening filter 10 and the outer protective cover 30 is lower than the absolute value of each of the inner protective cover 20, the darkening filter 10 and the outer protective cover 30 individually.

Other dimensions are possible as appropriate. The refractive power of the eye protection shield or its components may be calculated in accordance with Gullstrand's afocal lens formula:

$$\frac{1}{f} = (n-1)\left[\frac{1}{R_1} - \frac{1}{R_2} + \frac{(n-1)d}{nR_1R_2}\right],$$

In which "n" is the refractive index of the material of the eye protection shield and its components, R1 is the radius of the outer surface, R2 is the radius of the inner surface and d is the thickness of the eye protection shield or its components. It is noted that R2 for the eye protection shield or its components is a negative value because it refers to the radius of a concave surface, whereas R1 refers to the radius of a convex surface.

The invention claimed is:

1. A curved eye protection shield for welding protection, comprising a curved electrically switchable darkening filter and a protective cover comprising a first protective cover and a second protective cover, the darkening filter having an eye facing major inner surface and, opposite thereof, a major outer surface, and wherein the first protective cover is disposed on or adjacent to the eye facing major inner surface and the second protective cover is disposed on or adjacent to the major outer surface of the darkening filter, wherein each of the first and second protective covers includes a major inner surface and, opposite thereof, further a major outer surface, wherein inner major surface of the second protective cover and the outer major surface of the first protective cover faces the respective outer or inner major surfaces of the darkening filter, and wherein the inner and outer surface of the darkening filter are equidistant, whereas the inner and outer surface of at least one of the first and second protective covers are non-equidistant, wherein the arrangement of at least one of the first and second protective covers compensates for a refractive power of the curved darkening filter.

2. The curved eye protection shield of claim 1, wherein at least one of the first and second protective covers is pre-shaped so that either the outer surface of the protective cover corresponds in shape to the inner surface of the darkening filter or to a proportionally reduced shape of the inner surface of the darkening filter, or the inner surface of the protective cover corresponds in shape to the outer surface of the darkening filter or to a proportionally enlarged shape to the inner surface of the darkening filter.

3. The curved eye protection shield of claim 1, wherein at least one of the first and second protective covers has a first thickness adjacent a margin and a second thickness in the middle between two opposite margins, and wherein the second thickness is greater than the first thickness.

4. The curved eye protection shield of claim 1, wherein the inner and outer surface of the darkening filter are cylindrical and concentric relative to each other.

5. The curved eye protection shield of claim 4, wherein the inner and outer surface of at least one of the first and second protective covers are cylindrical, wherein the cylinder shape of the inner and outer surface of at least one of the first and second protective covers are in an off-center relationship to each other.

6. The curved eye protection shield of claim 5, wherein the cylindrical shape of the inner and outer surface of at least one of the first and second protective covers are based on the same radius within a range of 70 mm to 150 mm, wherein the center axes of the cylindrical shape of each the inner and outer surface of at least one of the first and second protective covers are preferably parallel offset from each other on a normal on the inner and outer surface with the offset being within a range of 0.5 mm to 3 mm.

7. The curved eye protection shield of claim 1, wherein at least one of the first and second protective covers is removably attached relative to the darkening filter.

8. The curved eye protection shield of claim 1, wherein the darkening filter and at least one of the first and second protective covers are arranged with a space between the inner surface of the darkening filter and the outer surface of the first protective cover or between the outer surface of the darkening filter and the inner surface of the second protective cover.

9. The curved eye protection shield of claim 1, wherein at least one of the first and second protective covers is made of a plastic material selected from among polycarbonate (PC), polymethyl methacrylate (PMMA), polystyrene (PS) and styrene acrylonitrile copolymer (SAN).

10. A welding protector comprising the curved eye protection shield of claim 1 and a non-transparent head protection shield, wherein the head protection shield forming a window which is closed by the curved eye protection shield.

11. The curved eye protection shield of claim 1, wherein the inner and outer surface of the first protective cover are shaped to compensate for the refractive power of the darkening filter.

12. A method of retrofitting a welding protector which has a curved eye protection shield, the eye protection shield comprising a curved electrically switchable darkening filter, the darkening filter having an eye facing major inner surface and, opposite thereof, a major outer surface, wherein the inner and outer surface of the darkening filter are equidistant, the method comprising the steps of (i) providing a first protective cover having a major inner surface and further a major outer surface, wherein the inner and outer surface of the first protective cover are non-equidistant and (ii) mounting the first protective cover relative to the darkening filter such that the outer surface of the first protective cover faces the inner surface of the darkening filter and (iii) providing a second protective cover having a major inner surface and further a major outer surface such that the inner surface of the second protective cover faces the outer surface of the darkening filter, wherein the arrangement of at least one of the first and second protective covers compensates for a refractive power of the curved darkening filter.

\* \* \* \* \*